(12) United States Patent
Sarpeshkar et al.

(10) Patent No.: US 10,297,835 B2
(45) Date of Patent: May 21, 2019

(54) FLEXIBLE AND IMPLANTABLE GLUCOSE FUEL CELL

(71) Applicants: Rahul Sarpeshkar, Arlington, MA (US); Jeremy Bert Muldavin, Arlington, MA (US); Todd Addison Thorsen, Carlisle, MA (US); Jakub Kedzierski, Nashua, NH (US); Benjamin Isaac Rapoport, New York, NY (US); Michale Sean Fee, Lexington, MA (US)

(72) Inventors: Rahul Sarpeshkar, Arlington, MA (US); Jeremy Bert Muldavin, Arlington, MA (US); Todd Addison Thorsen, Carlisle, MA (US); Jakub Kedzierski, Nashua, NH (US); Benjamin Isaac Rapoport, New York, NY (US); Michale Sean Fee, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 565 days.

(21) Appl. No.: 14/278,478

(22) Filed: May 15, 2014

(65) Prior Publication Data

US 2014/0342247 A1    Nov. 20, 2014

Related U.S. Application Data

(60) Provisional application No. 61/824,647, filed on May 17, 2013.

(51) Int. Cl.
*A61N 1/378*     (2006.01)
*H01M 4/86*      (2006.01)
(Continued)

(52) U.S. Cl.
CPC ........ *H01M 4/8652* (2013.01); *A61N 1/3785* (2013.01); *H01M 4/8626* (2013.01);
(Continued)

(58) Field of Classification Search
None
See application file for complete search history.

(56) References Cited

U.S. PATENT DOCUMENTS 3,861,397 A    1/1975    Rao et al.
3,941,135 A    3/1976    von Sturm et al.
(Continued)

FOREIGN PATENT DOCUMENTS

WO    2011117357 A2    9/2011

OTHER PUBLICATIONS

Ryu et al., Carbon Nanotubes With Platinum Nano-Islands As Glucose Biofuel Cell Electrodes, Biosensors and Bioelectronics, 2010, 25(7): 1603-1608.*

(Continued)

*Primary Examiner* — Robert S Carrico
(74) *Attorney, Agent, or Firm* — Quarles & Brady LLP (57) ABSTRACT

A glucose fuel cell for reception into a given constrained volume of implantation in a vertebrate in which the glucose fuel cell has access to fluid containing glucose. The fuel cell includes an anode adapted to oxidize the glucose, a cathode adapted to reduce an oxidant, and a membrane disposed between the anode and the cathode and separating the anode from the cathode. At least one of the anode or cathode define a flexible sheet that is geometrically deformed to be receivable into the given constrained volume of implantation and increase volumetric power density. Related methods of making a glucose fuel cell of this type and implantable assemblies including the glucose fuel cell are also disclosed.

14 Claims, 6 Drawing Sheets

(51) Int. Cl.

| | |
|---|---|
| H01M 4/90 | (2006.01) |
| H01M 4/92 | (2006.01) |
| H01M 4/98 | (2006.01) |
| H01M 8/00 | (2016.01) |
| H01M 8/1009 | (2016.01) |
| H01M 8/1039 | (2016.01) |
| H01M 8/1097 | (2016.01) |
| H01M 8/1018 | (2016.01) |
| A61B 5/00 | (2006.01) |
| A61B 5/145 | (2006.01) |
| H01M 8/1069 | (2016.01) |
| H01M 8/1081 | (2016.01) |
| H01M 4/88 | (2006.01) |
| H01M 8/0208 | (2016.01) |

(52) U.S. Cl.
CPC .......... *H01M 4/8663* (2013.01); *H01M 4/90* (2013.01); *H01M 4/921* (2013.01); *H01M 4/98* (2013.01); *H01M 8/004* (2013.01); *H01M 8/1009* (2013.01); *H01M 8/1039* (2013.01); *H01M 8/1097* (2013.01); *A61B 5/14532* (2013.01); *A61B 5/686* (2013.01); *H01M 4/8867* (2013.01); *H01M 4/8882* (2013.01); *H01M 8/0208* (2013.01); *H01M 8/1076* (2013.01); *H01M 8/1081* (2013.01); *H01M 2008/1095* (2013.01); *Y02P 70/56* (2015.11)

(56) References Cited

U.S. PATENT DOCUMENTS

| | | | | |
|---|---|---|---|---|
| 4,500,395 A * | 2/1985 | Nakamura | .......... | H01M 4/8807 204/284 |
| 2008/0213631 A1* | 9/2008 | Krishnamoorthy | .......................... | H01M 8/04208 429/2 |
| 2014/0004427 A1* | 1/2014 | Medoff | .................... | H01M 8/16 429/401 |
| 2014/0322617 A1* | 10/2014 | Wang | .................. | H01M 4/9008 429/401 |

OTHER PUBLICATIONS

Kerzenmacher, S. et al. "A Surface Mountable Glucose Fuel Cell for Medical Implants." Transducers 2007—2007 International Solid-State Sensors, Actuators and Microsystems Conference, 2007, IEEE, doi:10.1109/sensor.2007.4300087.*
Attard, et al., Liquid-Crystal Templates for Nanostructured Metals, Angewandte Chemie International Edition in English, 1997, 36(12):1315-1317.
Collins, et al., Deep Brain Stimulation for Movement Disorders, Neurobiology of Disease, 2010, 38(3):338-345.
Devi, et al., Dimensions of the Lumbar Vertebral Canal, Indian Journal of Orthopaedics, 2003, 37(3):186-188.
Fan, et al., Permeability of Glucose and Other Neutral Species Through Recast Perfluorosulfonated Ionomer Films, Anal. Chem., 1992, 64(11):1304-1311.
Gebhardt, et al., A Special Type of Raney-Alloy Catalyst Used in Compact Biofuel Cells, Journal of Applied Electrochemistry, 1976, 6(2):127-134.
Giner, et al., Electrochemical Glucose Oxidation on a Platinized Platinum Electrode in Krebs-Ringer Solution: IV. Effect of Amino Acids, J. Electrochem. Soc., 1981, 128(10)2106-2114.
Hahnloser, et al., An Ultra-Sparse Code Underlies the Generation of Neural Sequences in a Songbird, Nature, 2002, 419:65-70.
Halamkova, et al., Implanted Biofuel Cell Operating in a Living Snail, J. Am. Chem. Soc., 2012, 134(11):5040-5043.
Kerzenmacher, et al., Energy Harvesting by Implantable Abiotically Catalyzed Glucose Fuel Cells, Journal of Power Sources, 2008, 182(1):1-17.
Kim, et al., Bacterial Adhesion, Cell Adhesion and Biocompatibility of Nafion Films, Journal of Biomaterials Science, 2009, 20(12):1687-1707.
Lee, et al., Fully Packaged Nonenzymatic Glucose Microsensors with Nanoporous Platinum Electrodes for Anti-Fouling, IEEE Sensors Journal, 2008, 8(11):1922-1927.
Leung, et al., Chapter Nine—Peptide Nanofiber Scaffold for Brain Tissue Reconstruction, Methods in Enzymology, 2012, 508:177-190.
Long, et al. Using Temperature to Analyse Temporal Dynamics in the Songbird Motor Pathway, Nature, 2008, 456:189-194.
Long, et al., Support for a Synaptic Chain Model of Neuronal Sequence Generation, Nature, 2010, 468:394-399.
Lu, et al., Cerebral Autoregulation and Gas Exchange Studied Using a Human Cardiopulmonary Model, American Journal of Physiology—Heart and Circulatory Physiology, 2004, 286(2):H584-H601.
Nicolelis, Brain-Machine Interfaces to Restore Motor Function and Probe Neural Circuits, Nature Reviews Neuroscience, 2003, 4:417-422.
Ommaya, Implantable Devices for Chronic Access and Drug Delivery to the Central Nervous System, Cancer Drug Delivery, 1984, 1(2):169-179.
Osman, et al., Recent Progress and Continuing Challenges in Bio-Fuel Cells. Part II: Microbial, Biosensors and Bioelectronics, 2010, 26(3):953-963.
Prilutsky, et al., Anodes for Glucose Fuel Cells Based on Carbonized Nanofibers with Embedded Carbon Nanotubes, Electrochimica Acta, 2010, 55(11):3694-3702.
Rao, et al., Electrochemical Behavior of Amino Acids and Their Influence on the Anodic Oxidation of Glucose in Neutral Media, Biomat. Med. Dev. Art. Org., 1978, 6(2):127-149.
Rishpon, et al., Amperometric Glucose Sensors Based on Glucose Oxidase Immobilized in Nafion, Electroanalysis, 1994, 6(1):17-21.
Salthouse, et al., A Micropower Band-Pass Filter for Use in Bionic Ears, IEEE International Symposium on Circuits and Systems, 2002, 5:V189-V192.
Sarpeshkar, Brain Power—Borrowing From Biology Makes for Low Power Computing, IEEE Spectrum, 2006, 43 (5):24-29.
Sharrock, et al., Biological Fuel Cell Incorporating a Selective Anode Catalyst, Analytical Letters, 1976, 9 (12):1085-1090.
Smith, et al., An Externally Powered, Multichannel, Implantable Stimulator for Versatile Control of Paralyzed Muscle, IEEE Transactions on Biomedical Engineering, 1987, BME-34(7):499-508.
Song, et al., Rapid Fabrication of Microfluidic Polymer Electrolyte Membrane Fuel Cell in PDMS by Surface Patterning of Perfluorinated Ion-Exchange Resin, Journal of Power Sources, 2008, 183(2):674-677.
Turicchia, et al., A Low-Power Imager and Compression Algorithms for a Brain-Machine Visual Prosthesis for the Blind, Proceedings of SPIE, 2008, 7035:703510-1-703510-13.
Wong, et al., A Very Low-Power CMOS Mixed-Signal IC for Implantable Pacemaker Applications, IEEE Journal of Solid State Circuits, 2004, 39(12):2446-2456.
Wu, et al., Carbon Nanotube Supported Pt Electrodes for Methanol Oxidation: A Comparison Between Multi- and Single-Walled Carbon Nanotubes, Journal of Power Sources, 2007, 174(1):148-158.
Zaharchuk, et al., Measurement of Cerebrospinal Fluid Oxygen Partial Pressure in Humans Using MRI, Magnetic Resonance in Medicine, 2005, 54(1):113-121.
Zhak, et al., A Low-Power Wide Dynamic Range Envelope Detector, IEEE Journal of Solid State Circuits, 2003, 38 (10):1750-1753.
Zoll, Resuscitation of the Heart in Ventricular Standstill by External Electric Stimulation, N. Engl. J. Med., 1952, 247:768-771.
Weidlich, et al., Animal Experiments with Biogalvanic and Biofuel Cells, Biomat. Med. Dev. Art. Org., 1976, 4 (3&4):277-306.
Andrew, et al., Microfluidic Temporal Cell Stimulation, Twelfth International Conference on Miniaturized Systems for Chemistry and Life Sciences, 2008, pp. 674-676
Arfin, et al., Wireless Neural Stimulation in Freely Behaving Small Animals, J. Neurophysiol., 2009, 102:598-605.

(56) References Cited

OTHER PUBLICATIONS

Arfin, et al., An Energy-Efficient, Adiabatic Electrode Stimulator With Inductive Energy Recycling and Feedback Current Regulation, IEEE Transactions on Biomedical Circuits and Systems, 2012, 6(1):1-14.
Aronov, et al., Analyzing the Dynamics of Brain Circuits With Temperature: Design and Implementation of a Miniature Thermoelectric Device, J. Neurosci. Methods, 2011, 197(1):32-47.
Attard, et al., Mesoporous Platinum Films From Lyotropic Liquid Crystalline Phases, Science, 1997, 278:838-840.
Baker, et al., A Low-Power High-PSRR Current-Mode Microphone Preamplifier, IEEE Journal of Solid State Circuits, 2003, 38(10):1671-1678.
Baker, et al., Feedback Analysis and Design of RF Power Links for Low-Power Bionic Systems, IEEE Transactions on Biomedical Circuits and Systems, 2007, 1(1):28-38.
Bullen, et al., Biofuel Cells and Their Development, Biosensors and Bioelectronics, 2006, 21:2015-2045.
Davis, et al., Biofuelcells—Recent Advances and Applications, Biosensors and Bioelectronics, 2007, 22(7):1224-1235.
Do Valle, et al., An Area and Power-Efficient Analog Li-Ion Battery Charger Circuit, IEEE Transactions on Biomedical Circuits and Systems, 2011, 5(2):131-137.
Drake, et al., A Tissue Implantable Fuel Cell Power Supply, Trans. Amer. Soc. Artif. Int. Organs, 1970, 16:199-205.
Ellis-Behnke, et al., Nano Neuro Knitting: Peptide Nanofiber Scaffold for Brain Repair and Axon Regeneration With Functional Return of Vision, PNAS, 2006, 103(13):5054-5059.
Fay, et al., A Micropower Electrocardiogram Amplifier, IEEE Transactions on Biomedical Circuits and Systems, 2009, 3(5):312-320.
Fee, et al., Central Versus Peripheral Determinants of Patterned Spike Activity in Rat Vibrissa Cortex During Whisking, Journal of Neurophysiology, 1997, 78:1144-1149.
Fee, Active Stabilization of Electrodes for Intracellular Recording in Awake Behaving Animals, Neuron, 2000, 27:461-468.
Fee, et al., Miniature Motorized Microdrive and Commutator System for Chronic Neural Recording in Small Animals, Journal of Neuroscience Methods, 2001, 112:83-94.
Fee, et al., New Methods for Localizing and Manipulating Neuronal Dynamics in Behaving Animals, Curr. Opin. Neurobiol., 2011, 21(5):693-700.
Gold, et al., Acid Loaded Porous Silicon as a Proton Exchange Membrane for Micro-Fuel Cells, Journal of Power Sources, 2004, 135:198-203.
Guo, et al., Self-Assembling Peptide Nanofiber Scaffold Promotes the Reconstruction of Acutely Injured Brain, Nanomedicine: Nanotechnology, Biology, and Medicine, 2009, 5:345-351.
Heller, Miniature Biofuel Cells, Phys. Chem. Chem. Phys., 2004, 6:209-216.
Helmchen, et al., A Miniature Head-Mounted Two-Photon Microscope: High-Resolution Brain Imaging in Freely Moving Animals, Neuron, 2001, 31:903-912.
Hochberg, et al., Neuronal Ensemble Control of Prosthetic Devices by a Human with Tetraplegia, Nature, 2006, 442:164-171.
Kerzenmacher, et al., Raney-Platinum Film Electrodes for Potentially Implantable Glucose Fuel Cells. Part 1: Nickel-Free Glucose Oxidation Anodes, Journal of Power Sources, 2010, 195:6516-6523.
Lam, et al., Culturing Aerobic and Anaerobic Bacteria and Mammalian Cells with a Microfluidic Differential Oxygenator, Anal. Chem., 2009, 81:5918-5924.
Linderoth, et al., Physiology of Spinal Cord Stimulation: Review and Update, Neuromodulation, 1999, 2(3):150-164.
Luo, et al., Encoding Pheromonal Signals in the Accessory Olfactory Bulb of Behaving Mice, Science, 2003, 299:1196-1201.
Mandal, et al., Low Power CMOS Rectifier Design for RFID Applications, IEEE Transactions on Circuits and Systems, Regular Papers, 2007, 54(6):1177-1188.
Mandal, et al., Power-Efficient Impedance-Modulation Wireless Data Links for Biomedical Implants, IEEE Transactions on Biomedical Circuits and Systems, 2008, 2(4):301-315.
Mandal, et al., A Bio-Inspired Active Radio-Frequency Silicon Cochlea, IEEE Journal of Solid State Circuits, 2009, 44 (6):1814-1828.
Niessen, et al., Exploiting Complex Carbohydrates for Microbial Electricity Generation—A Bacterial Fuel Cell Operating on Starch, Electrochemistry Communications, 2004, 6:955-958.
Normann, et al., A Neural Interface for a Cortical Vision Prosthesis, Vision Research, 1999, 39:2577-2587.
Patil, Introduction: Advances in Brain-Machine Interfaces, Neurosurg. Focus, 2009, 27(1):E1, 2 pages.
Perry, et al., The Amino Acid Content of Human Cerebrospinal Fluid in Normal Individuals and in Mental Defectives, Journal of Clinical Investigation, 1961, 40:1363-1372.
Rabaey, et al., Biofuel Cells Select for Microbial Consortia That Self-Mediate Electron Transfer, Applied and Environmental Microbiology, 2004, 70(9):5373-5382.
Rapoport, et al., A Biomimetic Adaptive Algorithm and Low-Power Architecture for Implantable Neural Decoders, Conf. Proc. IEEE Eng. Med. Biol. Soc., 2009, 2009:4214-4217.
Rapoport, et al., A Glucose Fuel Cell for Implantable Brain-Machine Interfaces, PLoS One, 2012, 7(6):e38436, pp. 1-15.
Rapoport, et al., Efficient Universal Computing Architectures for Decoding Neural Activity, PLoS One, 2012, 7(9): e42492, pp. 1-13.
Sarpeshkar, et al., An Ultra-Low-Power Programmable Analog Bionic Ear Processor, IEEE Transactions on Biomedical Engineering, 2005, 52(4):711-727.
Sarpeshkar, et al., Low-Power Circuits for Brain-Machine Interfaces, IEEE Transactions on Biomedical Circuits and Systems, 2008, 2(3):173-183.
Sarpeshkar, Universal Principles for Ultra Low Power and Energy Efficient Design, IEEE Transactions on Circuits and Systems II: Express Briefs, 2012, 59(4):193-198.
Schwartz, et al., Brain-Controlled Interfaces: Movement Restoration with Neural Prosthetics, Neuron, 2006, 52:205-220.
Sharma, et al., Mesoporous Silica as a Membrane for Ultra-Thin Implantable Direct Glucose Fuel Cells, Lab Chip, 2011, 11:2460-2465.
Sit, et al., A Micropower Logarithmic A/D With Offset and Temperature Compensation, IEEE Journal of Solid State Circuits, 2004, 39(2):308-319.
Sit, et al., A Cochlear-Implant Processor for Encoding Music and Lowering Stimulation Power, IEEE Pervasive Computing, 2008, 1(7):40-48.
Thies, et al., Abstraction Layers for Scalable Microfluidic Biocomputing, Nat. Comput, 2008, 7:255-275.
Urbanski, et al., Digital Microfluidics Using Soft Lithography, Lab Chip, 2006, 6:96-104.
Urbanski, et al., Noninvasive Metabolic Profiling Using Microfluidics for Analysis of Single Preimplantation Embryos, Anal. Chem., 2008, 80(17):6500-6507.
Wattanapanitch, et al., An Energy-Efficient Micropower Neural Recording Amplifier, IEEE Transactions on Biomedical Circuits and Systems, 2007, 1(2):136-147.
Wattanapanitch, et al., A Low-Power 32-Channel Digitally Programmable Neural Recording Integrated Circuit, IEEE Transactions on Biomedical Circuits and Systems, 2011, 5(6):592-602.
PCT International Search Report and Written Opinion, PCT/US2014/038090, dated Aug. 22, 2014, 13 pages.

* cited by examiner

FIG. 6

FLEXIBLE AND IMPLANTABLE GLUCOSE FUEL CELL

CROSS-REFERENCE TO RELATED APPLICATIONS

This application claims the benefit of U.S. provisional patent application Ser. No. 61/824,647 filed on May 17, 2013, the contents of which are incorporated by reference for all purposes as if set forth in their entirety herein.

STATEMENT OF FEDERALLY SPONSORED RESEARCH OR DEVELOPMENT

This invention was made with Government support under Grant No. R01 NS056140 awarded by the National Institutes of Health and by Grant No. 1332250 awarded by the National Science Foundation. The United States Government has certain rights in the invention.

BACKGROUND

This invention relates to glucose fuel cells for use in the body. In particular, this invention relates to improvements in the volumetric power densities of glucose fuel cells.

In a glucose-based biofuel cell, glucose is oxidized at the anode, while oxygen is reduced to water at the cathode. The nature of the catalyst residing at the anode influences the extent of glucose oxidation and the associated oxidation products.

Three major design paradigms for glucose-based fuel cells exist, with numerous design examples described in patent and scientific literature, differing principally in the materials used to catalyze electrode reactions. In a first paradigm, the catalysts are isolated enzymes that are fixed to electrode substrates. In a second paradigm, oxidation is performed by exoelectrogenic bacteria, in biofilms, that colonize a fuel cell anode. In a third paradigm, the catalysts are abiotic, solid-state materials.

Enzyme-based glucose fuel cells have high catalytic efficiency which, together with their small size, results in high volumetric power density, yielding up to 4.3 µW of total power in systems with footprints on the order of 1 mm$^2$ and volumes less than $10^{-2}$ mm$^3$. Such fuel cells are often constructed as tethered-enzyme systems, in which oxidation and reduction of fuel cell substrates are catalyzed ex vivo by enzymes molecularly wired to threads of conductive material. Enzyme-based glucose fuel cells described in the recent literature have typically generated on the order of 100 µW·cm$^{-2}$. Fuel cells of this kind may be capable of continuous operation for up to several weeks. However, their lifetimes are often limited by the tendency of the enzymes to degrade and ultimately degenerate with time. This characteristic of enzymes is one of the main reasons why the body constantly makes and degrades enzymes, such that the enzymes never lose their efficacy.

Using living microorganisms, such as exoelectrogenic bacteria, to catalyze the anodic reaction results in complete oxidation of glucose, liberating twenty-four electrons per molecule of glucose consumed. Microbial fuel cells are therefore very catalytically efficient and can produce more than 1900 µW·cm$^{-2}$. In contrast with enzymatic systems, which have shorter lifetimes and are limited by the degradation of tethered enzymes ex vivo, microbial fuel cells are inherently self-regenerating as microbial fuel cells use a fraction of the input biomass to power and supply molecular substrates for maintenance functions such as resynthesis of degraded enzymes. Microbial glucose fuel cells described in the recent literature have typically generated on the order of 1000 µW·cm$^{-2}$. However, the prospect of implanting even non-pathogenic bacteria raises concerns of safety and biocompatibillty. Thus, microbial fuel cells of the present generation are not yet suitable for biologically implanted applications.

Figure 1A:
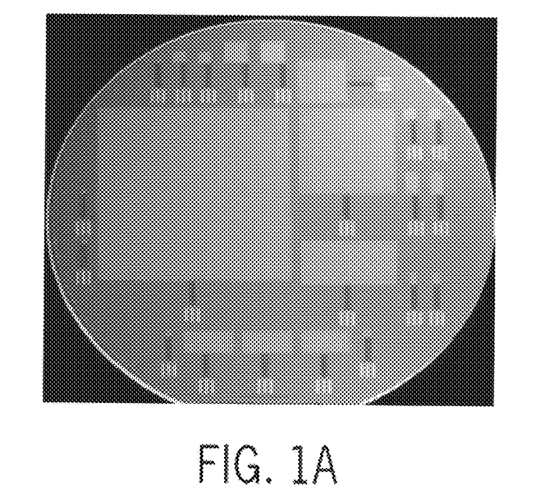
FIG. 1A is a silicon wafer having glucose fuel cells of various areas fabricated on the wafer.
Figure 1B:
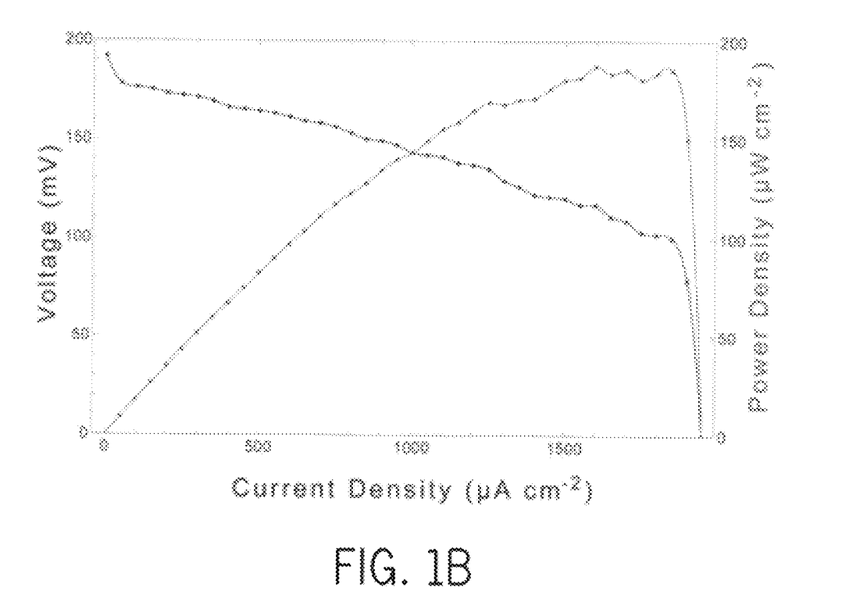
FIG. 1B is a current-voltage curve for a glucose fuel cell shown in FIG. 1.

Solid-state anode catalysts are capable of oxidizing glucose to gluconic acid, liberating one pair of electrons, and yielding further oxidation products with reduced probability. As a result, solid-state catalysts represent the least catalytically efficient of the three design paradigms identified above. While glucose fuel cells based on solid-state catalysts typically only generate 1 to 10 µW·cm$^{-2}$, they have proven reliable as implantable power sources in animals for several months due to their use of biocompatible materials. FIG. 1A illustrates biocompatible glucose fuel cells of various cross-sectional areas fabricated on a rigid silicon wafer substrate. As shown in FIG. 1B, one of the glucose fuel cells fabricated on the wafer generated an open circuit voltage of 192 mV, with steady state power of 3.8 µW·cm$^{-2}$ and transient peak power levels in excess of 180 µW·cm$^{-2}$ at 1.5 to 1.85 mA·cm$^{-2}$. However, these power levels are still relatively small.

Hence, a need exists for biocompatible glucose fuel cells having improved volumetric power density for use in the human body for relatively long durations of time.

SUMMARY OF THE INVENTION

In this invention, a flexible and implantable glucose fuel cell is disclosed having improved volumetric power density by an order of magnitude over prior designs. During fabrication, the underlying substrate as well as at least one of the anode and cathode is produced in such a way that they have exceptional flexibility. This flexibility enables the construction of high-surface-area electrodes that fit within a small volume thus improving volumetric limits on oxidation or reduction current density at the electrode. Miniature prosthetic systems that function with needed steady-state power budgets can then be built to run on these fuel cells. Techniques that exploit resonant transformer action and efficient rectification may be used to efficiently convert even 20 mV energy-harvesting outputs to the 1-5 V levels needed for powering electronic chips.

According to one aspect, a glucose fuel cell is disclosed for reception into a given constrained volume of implantation in a vertebrate in which the glucose fuel cell has access to cerebrospinal fluid including glucose. The fuel cell comprises an anode adapted to oxidize the glucose, a cathode adapted to reduce an oxidant, and a membrane. The membrane is disposed between the anode and the cathode and separates the anode from the cathode. At least one of the anode and the cathode, define a flexible sheet that is geometrically deformed into a shape of the glucose fuel cell that is receivable into the given constrained volume of implantation. In some 'air cathode' implementations, the cathode may simply be exposed to the surrounding environment and separated from the anode via a stiff membrane but the anode is flexible. In other implementations, the anode, cathode, and membrane may all be flexible and may be part of the flexible sheet.

The flexible sheet of the glucose fuel cell may further have openings that accommodate fluid flow from one side of the flexible sheet to the other side of the flexible sheet. The openings may extend through at least one of the anode, the cathode, and the membrane.

In some forms, the flexible sheet may further comprise a flexible mechanical substrate on which the anode, the cathode, and the membrane reside. The flexible sheet may be approximately 7 μm thick. The flexible mechanical substrate may be an oxide layer.

The flexible sheet may be rolled such that the glucose fuel cell has a rolled-up form factor. In this form, the form factor may be substantially cylindrical. However, the flexible sheet may be deformed or folded in other ways alternatively from rolling or in addition to rolling. As the flexible shape is deformed into a substantially three-dimensional shape, a volumetric power density of the fuel cell can be increased by increasing the reactive surface area of any of the electrodes in the cell within the specified volume or space.

In one specific form, the anode may be nanoporous platinum, the cathode may be a sulfonated tetrafluoroethylene based fluoropolymer-copolymer (such as Nafion® available from DuPont™) having single-walled carbon nanotubes embedded therein, and the membrane may be a sulfonated tetrafluoroethylene based fluoropolymer-copolymer (such as Nafion® available from DuPont™). It is contemplated that one or more of the anode, the cathode, and the membrane might be made with other materials. Moreover, it is contemplated that in forming the nanoporous platinum, another material, such as for example aluminum, may be etched away from a bi-metallic starting material and that, in such an event, trace amounts of the sacrificial material or other materials may remain in the anode. Similarly, the anode can be made from platinized platinum to have high surface area via electrodeposition techniques that make it reticulate.

The given constrained volume of implantation may be in a natural anatomic reservoir or an artificial, implanted reservoir with access to cerebrospinal fluid around the brain or the spinal cord of the vertebrate, or to other glucose-containing fluids within the body. The glucose fuel cell would then operate in cerebrospinal fluid with glucose being oxidized at the anode and dissolved oxygen (as the oxidant) being reduced at cathode to water.

According to another aspect, an implantable assembly includes the glucose fuel cell as described herein and further includes electronics powered by the glucose fuel cell. The glucose fuel cell may be co-fabricated with at least a portion of the electronics on a flexible mechanical substrate that is common to both the electronics and to the glucose fuel cell.

In the implantable assembly, the glucose fuel cell may provide one or more of power and glucose-sensing inputs to a medical device. The medical device might be implanted alongside the glucose fuel cell or might be implanted within the body at a location remote from a location of implantation of the glucose fuel cell.

According to still another aspect, a method of making a glucose fuel cell of the type described above is disclosed. The method includes depositing a first electrode layer of one of an anode and a cathode on an oxide layer of a substrate, such as a first silicon wafer. Then, a membrane is deposited on the first electrode layer. A second electrode layer of the other of the anode and the cathode is deposited on the membrane, such that the membrane is disposed between the anode and the cathode and separates the anode from the cathode. A carrier, such as a second silicon wafer, is bonded to the second electrode layer. The substrate is removed (by, for example, grinding), leaving the oxide layer in place as a flexible mechanical substrate. Once the carrier is released, this thereby forms a flexible sheet including the oxide layer, the anode, the cathode, and the membrane which is supported by the flexible mechanical substrate.

The method may further include the step of geometrically deforming the flexible sheet into a shape of the glucose fuel cell which is receivable into the given constrained volume of implantation. This step may involve rolling the flexible sheet such that the glucose fuel cell has a rolled-up form factor.

During at least one of the depositing steps, masks may be used which create openings in the flexible sheet. These openings may accommodate fluid flow from one side of the flexible sheet to the other side of the flexible sheet.

Thus, a thin flexible sheet for a glucose fuel cell and a glucose fuel cell are provided. In contrast to fuel cells using enzymes or microorganisms, this solid state material offers better biocompatibility without fouling when it is placed in and operated in cerebrospinal fluid. Because the thin flexible sheet can be readily deformed or rolled into a compact shape without breaking or harming the properties of the sheet, a high volumetric power density for the material can be obtained which enables the operation of medical devices.

These and still other advantages of the invention will be apparent from the detailed description and drawings. What follows is merely a description of some preferred embodiments of the present invention. To assess the full scope of the invention the claims should be looked to as these preferred embodiments are not intended to be the only embodiments within the scope of the claims.

DETAILED DESCRIPTION

Figure 2:
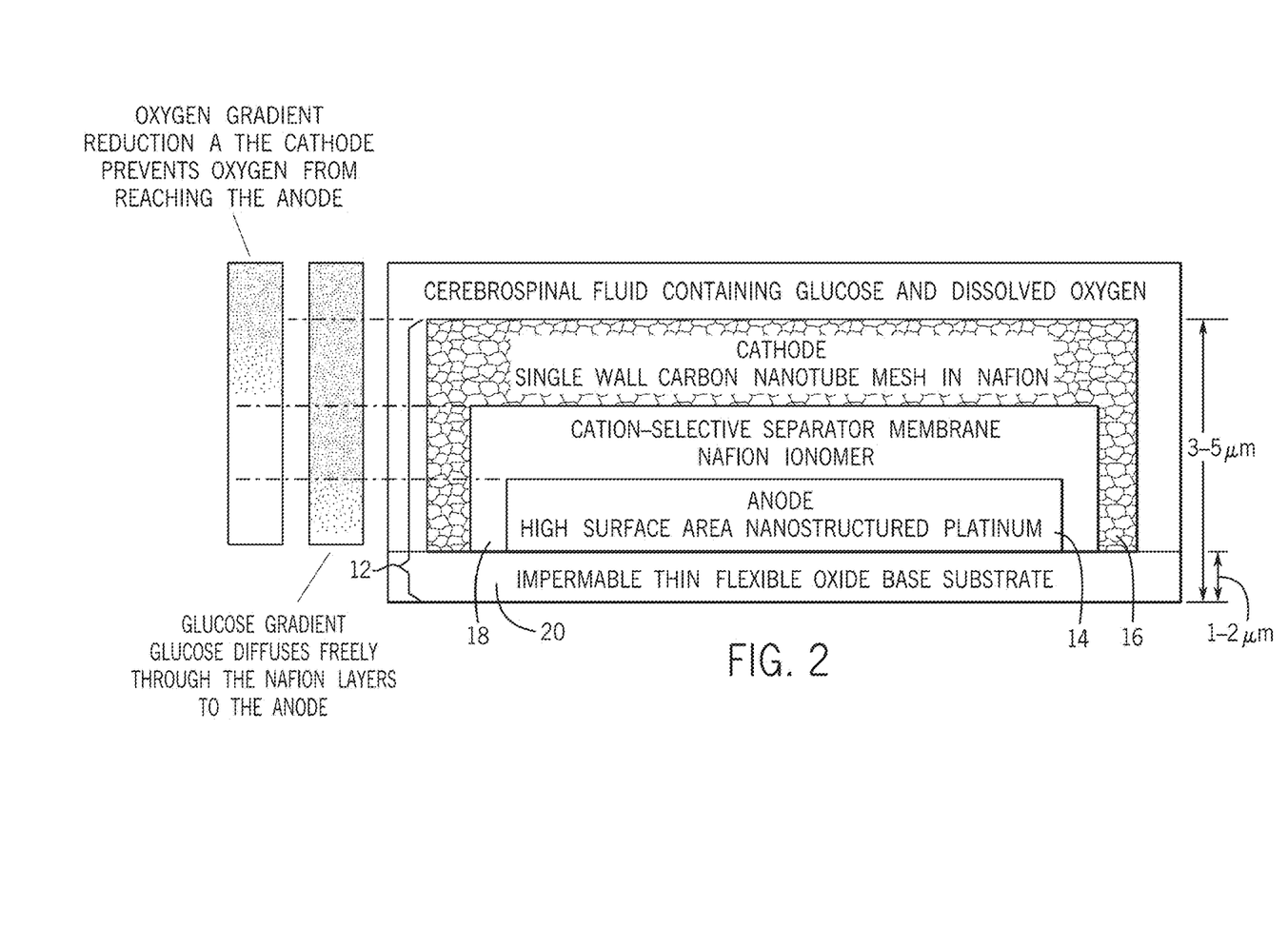
FIG. 2 is a cross-section of the glucose fuel cell schematically illustrating the structure of the fuel cell in surrounding body fluid, for example, cerebrospinal fluid, as well as the oxygen and glucose concentration gradients associated with its cathode and anode half-cell reactions, which are related to the overall fuel cell efficiency.
Figure 3:
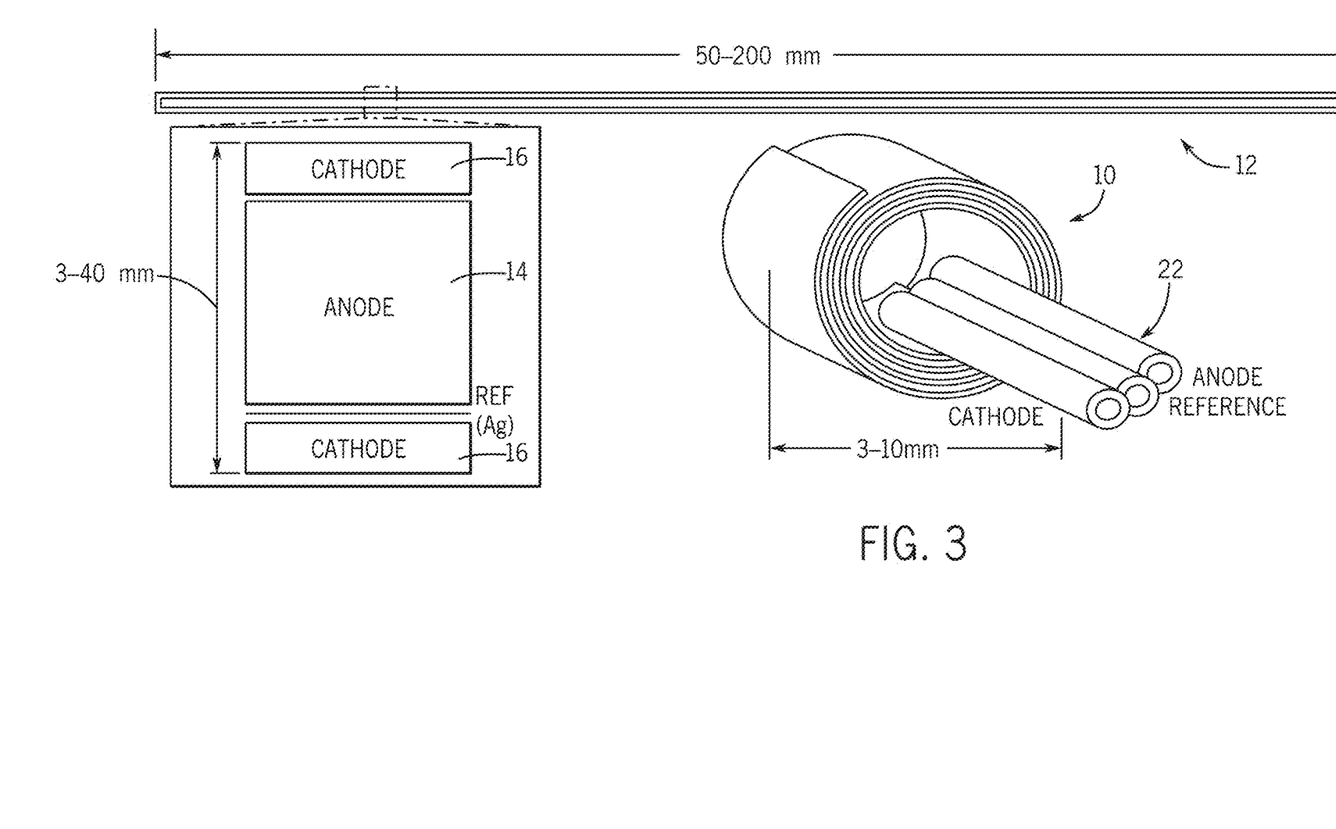
FIG. 3 shows a thin strip used (top) to form a glucose fuel cell in which leads are bonded to leads at contact electrode pads and, after the strip is subsequently rolled up, forms a coiled or rolled glucose fuel cell as illustrated on the bottom right for in vivo insertion.

Referring first to FIGS. 2 and 3, a solid-state glucose fuel cell design according to one aspect of the invention is illustrated. The solid state glucose fuel cell 10 uses a half-open, two-chamber design that is sized and shaped to fit a particular anatomic compartment, and is constructed using semiconductor fabrication techniques as will be described in greater detail below. To provide context for the description that follows, it is contemplated that this glucose fuel cell 10 may be received into a given constrained volume of implantation in a vertebrate in which the glucose fuel cell has access to cerebrospinal fluid including glucose. Among other things, cerebrospinal fluid contains glucose, but is relatively free from other substances that may foul the reactive surfaces of the fuel cell 10 and negatively impact the efficiency of the fuel cell 10. In such application, the glucose fuel cell 10 is relatively small in size and form factor having a footprint that does not exceed a few centimeters such that it may be implanted in a subcutaneous reservoir with access to cerebrospinal fluid in one or more of the brain or spinal cord of a vertebrate.

Unlike other glucose fuel cells such as, for example, a glucose fuel cell fabricated on an approximately 500 µm thick silicon wafer described above and illustrated in FIG. 1A, a flexible sheet or strip 12 from which the glucose fuel cell 10 is formed in FIGS. 2 and 3 is very thin and has a composition such that the sheet or strip 12 is geometrically deformable into a shape of the glucose fuel cell 10 that is receivable into the given constrained volume of implantation. As used herein, the term "flexible" means that the bending radius of the material is at least as small as the smallest dimension of the tightly constrained space (for example, a 1 cm diameter by 4 cm long volume) without causing the material to suffer substantial damage (for example, fracture). This also means that the material's thinnest dimension is substantially less than that of the overall volume for implantation such that surface-area-to-volume ratios will be improved when the material is implanted in the constraining space.

The flexible sheet or strip 12 includes an anode 14 that is adapted to oxidize glucose (such as glucose in the cerebrospinal fluid), a cathode 16 that is adapted to reduce an oxidant (such as dissolved oxygen in the cerebrospinal fluid to water), and a membrane 18 disposed between the anode 14 and the cathode 16 and separating the anode 14 from the cathode 16. The anode 14, the cathode 16 and the membrane 18 are all supported by and reside on a flexible mechanical substrate 20 such that the entire sheet or strip is substantially geometrically deformable into the shape of the glucose fuel cell 10 without damaging the various components. As best illustrated in FIG. 2, and as will be described in greater detail below with respect to the method of fabrication of the layers of the sheet or strip 12, the anode 14 is supported on top of the oxide layer of the flexible mechanical substrate 20 and the membrane 18 substantially covers the anode 14. A cathode 16 is supported on the other side of the membrane 18. As illustrated in the cross-section of FIG. 2, portions of all of the anode 14, the cathode 16, and the membrane 18 contact and are supported by the flexible mechanical substrate 20.

The flexible sheet 12 used to form the fuel cell 10 may be approximately 7 µm thick. The base layer or flexible mechanical substrate 20 of the glucose fuel cell comprises an ultra-thin oxide layer (only 1 to 2 µm thick) that is initially deposited on a thick silicon wafer substrate by plasma-enhanced chemical vapor deposition (PECVD), with the underlying silicon removed as an end process step by grinding and polishing after the fuel cell has been fabricated on the oxide surface of the thick silicon wafer as will be described in greater detail below. The thinned circuits and material of the anode 14, the cathode 16, and the membrane 16 are rugged, with a tensile strength comparable to metalized fiberglass, and have a sub-millimeter bending radius as illustrated in the left image of FIG. 6.

Now with specific reference to FIG. 3, the glucose fuel cell 10 is shown as initially being fabricated as a thin, long, generally linear strip 12. For the sake of clarity, the metal anode 14 and cathode 16 layers are shown in FIG. 3 without the membrane 18 layer. As illustrated, this strip 12 is 50 mm to 200 mm long and is 3 mm to 40 mm wide (and approximately 7 µm thick as described above). It is noted that these dimensions are for purposes of example only, and the exact dimensions and shape of the initial sheet or strip 12 can vary from these values and ranges.

The thin, long, generally linear strip 12 is then subsequently geometrically deformed into a shape of the fuel cell 10 or, more specific to the illustrated embodiment, rolled up into a rolled-up form factor as illustrated in the lower right of FIG. 3, thereby achieving a high volumetric power density and increasing the volumetric power density by virtue of increasing the available reactive surface area in the given volume of implantation for the fuel cell 10. Commercially available 90% Platinum—10% Indium biocompatible leads 22 are bonded to respective contact pads for the cathode, reference, anode at the end of each thread or strip 12, and the strip 12 of the fuel cell 10 is coiled around the leads 22, making it easy for in vivo insertion of the glucose fuel cell 10. For example, a 40 mm-width strip with a 200 mm nominal length, when rolled up into a cylinder that is 1 cm in diameter, can fit within a 1 cm diameter×4 cm subspace of a human at the bottom of the spinal cord in the lumbar cistern. Such a fuel cell has a working surface area of 80 cm$^2$, enabling 320 µW of power generation from a 4 µW/cm$^2$ device, which is twenty times greater than would have been possible using known cells without the use of such disclosed flexible sheets and strips.

Figure 4A:
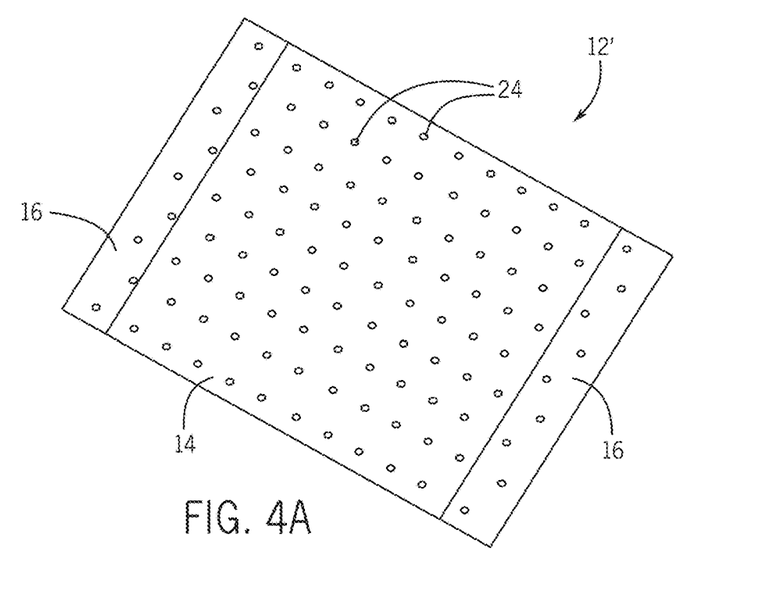
FIG. 4A shows a segment of a strip of a porous version of the fuel cell in planar form (prior to rolling), in which the strip is porous in the sense that it has openings or apertures that extend from one side of the flexible sheet to the other through one or more of the anode, the cathode, and the membrane.
Figure 4B:
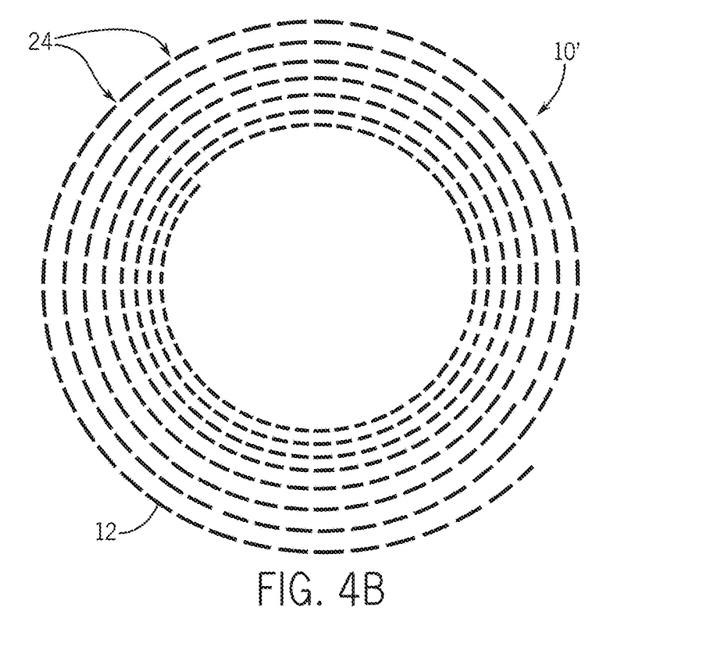
FIG. 4B illustrates a side cross-sectional view of the glucose fuel cell made from a strip of the porous version of the flexible sheet of FIG. 4A in which the cell has a rolled-up form factor in which the openings that accommodate fluid flow between the layers of the roll are illustrated as gaps.

To further increase glucose availability to the anode 14 and to automatically also increase oxygen availability to the cathode 16, the sheet or strip 12 can be formed with openings 24 as illustrated in FIGS. 4A and 4B that extend from one side of the strip or sheet 12' to the other side of the strip or sheet 12'. In this porous variant of the fuel cell 10' shown in FIG. 4B, the composite fuel cell 10' contains 25 µm by 25 µm square holes or openings 24 with a 250 µm pitch. These holes 24 allow glucose and oxygen radial access between coiled layers of the flexible sheet or strip 12 and accommodate fluid flow from one side of the flexible sheet or strip 12' to the other side of the flexible sheet or strip 12', particularly increasing cell performance in spiral or coiled geometries. These holes or openings 24 can extend through one or more of the anode 14, the cathode 16, and the membrane 18.

Figure 5:
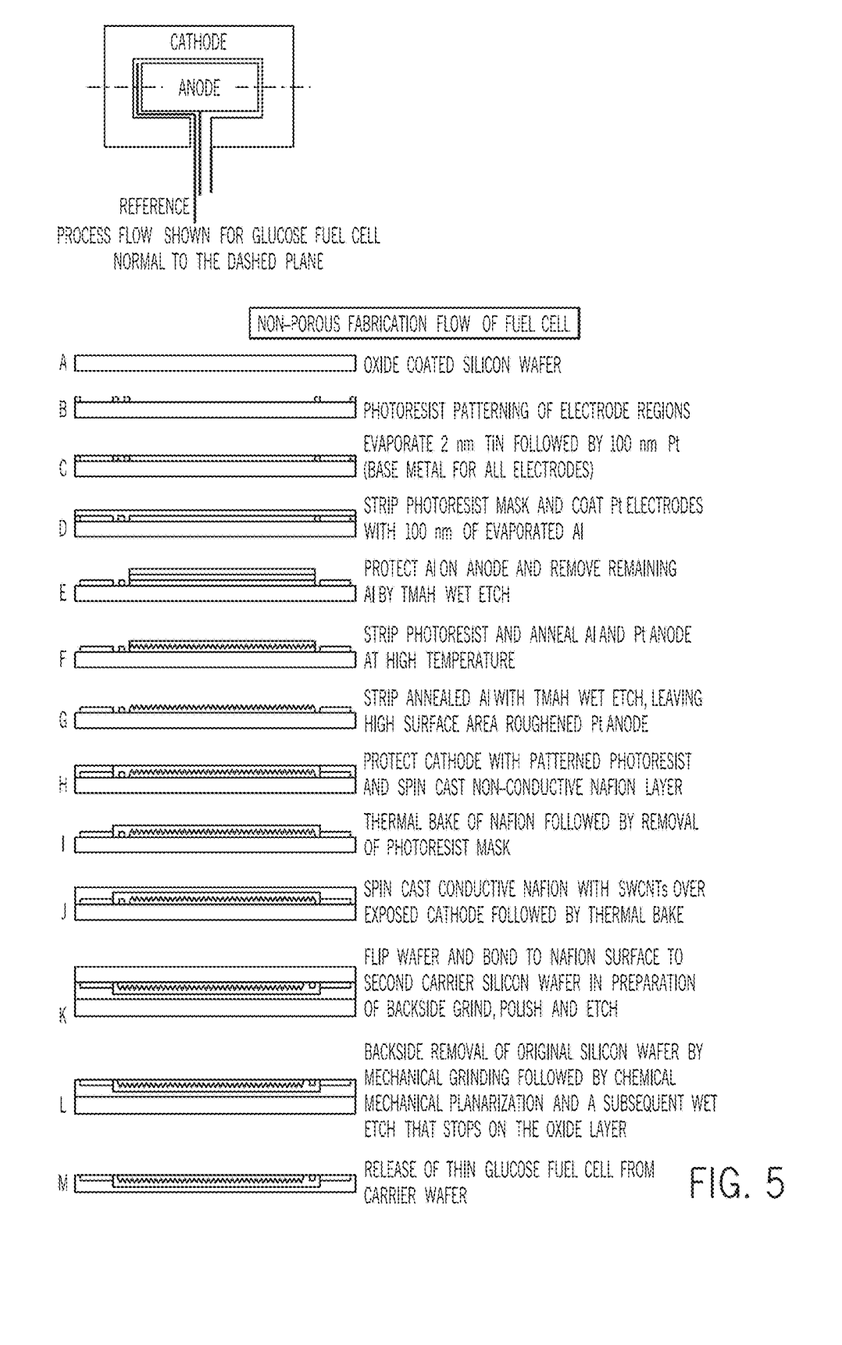
FIG. 5 is a step-by-step illustration of the fabrication process for production of a flexible sheet or strip that can be rolled or deformed to form the glucose fuel cell.

Turning now to FIG. 5, the fabrication of the flexible sheet or strip of the flexible composite glucose fuel cell 10 is illustrated for the non-porous embodiment. For the sake of clarity and to better reference the various steps in the fabrication process, each of the process steps are labeled A through M.

In step A, the process begins by obtaining a silicon wafer and coating the wafer with 2-3 µm of oxide deposited by plasma-enhanced chemical vapor deposition (PECVD).

It is noted that the fabrication process for a porous fuel cell (that is, a fuel cell of the type described and illustrated in FIG. 4 having openings or apertures) will include the same process steps as the non-porous version except that 25 µm by 25 µm square holes will be formed in the initial PECVD oxide using a separate mask and a dry etch process. It is contemplated that other sizes and shapes of holes could also be formed other than just 25 µm by 25 µm square holes. All of the non-porous lithography masks [electrodes, separator and Nafion® Single-Wall-Carbon-Nano-Tube (SW-CNT) cathode layer that will be described below] are modified to include features for the pores.

As illustrated in step B, all metal structures are initially patterned by applying a first photoresist mask that defines the anode, the cathode contact ring, wire traces, and electrical contacts. Next, in step C, 2 nm of TiN are deposited by evaporation followed by deposition of 100 nm of platinum by evaporation. In step D, the first photoresist mask is removed and 100 nm of aluminum are deposited over the entire surface of the wafer. In step E, a second photoresist mask is patterned over the regions designated for the anode (centrally shown on the wafer in FIG. 5). This second photoresist mask protects these anode regions from a tetramethylammonium hydroxide (TMAH) etchant that is also applied during step E that etches away the aluminum in all areas except for those designated as anodes.

In step F, after stripping the second photoresist mask, the platinum and aluminum layers are annealed at 300° C. for 60 minutes. This anneal step generates a platinum/aluminum alloy in the regions designated for the anodes. After annealing in step G, the aluminum etch step is repeated, this time without protecting the region of the anodes, in order to remove the aluminum from the platinum/aluminum alloy formed in the anode regions by the annealing. This second etch step produces roughened, high-surface-area Raney-type catalytic anodes. Other techniques such as electrodeposition of platinized platinum can also be used to increase surface area.

In step H, the areas to be coated with the membrane material, Nafion®, are first coated with 15-20 µm of photoresist (AZ 4620 available from AZ Electronic Materials) to create a third photoresist mask that is patterned so as to expose the regions to be coated with Nafion®. Using such thick layers of photoresist has been found to facilitate proper Nafion® patterning and lift-off by enabling patterned regions of Nafion® to be isolated in deep photoresist wells. Then, using a standard Nafion® liquid dispersion (Nafion® DE 521 available from Dupont™), an 0.83% solution (diluting the stock 1:5 in 2-propanol) is spin coated at 1000 rpm for 10 seconds to generate a Nafion® membrane film thicknesses of approximately 200 nm after a post-spin thermal bake at 120° C. for 20 minutes in step I. In step I, the third photoresist mask is also removed.

Before continuing with the description of the process, it is worth noting that the cathode of the illustrated glucose fuel cell comprises a conducting mesh of single-walled carbon nanotubes (swCNTs) embedded in Nafion®, which is in electrical contact with a platinum ring that defines the cathode contact on the wafer surface. The Nafion® with the embedded swCNTs forming the cathode will be separately deposited from the Nafion® separator membrane deposited in step H that is used to electrically insulate the cathode from the anode, while still permitting cationic exchange. However, both the separator membrane and the cathode permit ambient glucose to reach the anode surface, as Nafion® is inherently permeable to glucose and the porosity of the swCNT mesh allows free transport of glucose.

Now turning to step J, the Nafion®-coated swCNT mesh of the cathode will be constructed by allowing it to self-assemble. Previously synthesized and purified swCNTs (obtained from the Sigma-Aldrich Corporation) are suspended at a concentration of 8 mg·mL$^{-1}$ in an 0.83% Nafion® dispersion identical to that used for the separator membrane. Finally, the Nafion®-coated swCNT cathode is patterned with a fourth photoresist mask (not illustrated), with the deposition (using spin casting) and lift-off processes identical to those used to form the separator membrane.

After coating the glucose fuel cell with Nafion®, the fuel cell and attached wafer is flipped over and bonded to a carrier silicon wafer, as illustrated in step K, in anticipation of removal of the original silicon wafer substrate. Once the original silicon wafer substrate is removed, this ultimately produces an ultra-thin package (3-5 µm thick) with the fuel cell (including the anode, the membrane, and the cathode) supported by a base or flexible mechanical substrate of the original 1-2 µm thick PECVD oxide. The Nafion® face of the fuel cell is bonded to the carrier wafer using a bonding agent specially formulated for releasing thinned wafers compatible with Nafion® (Brewer Science WaferBond CR-200). In step L, the original silicon wafer is removed up to the oxide layer through a combination of mechanical grinding, chemical mechanical planarization, and finally a wet etch that stops on the oxide. After thinning, the carrier wafer is released in step M, leaving only the thin flexible glucose fuel cell.

Figure 6:
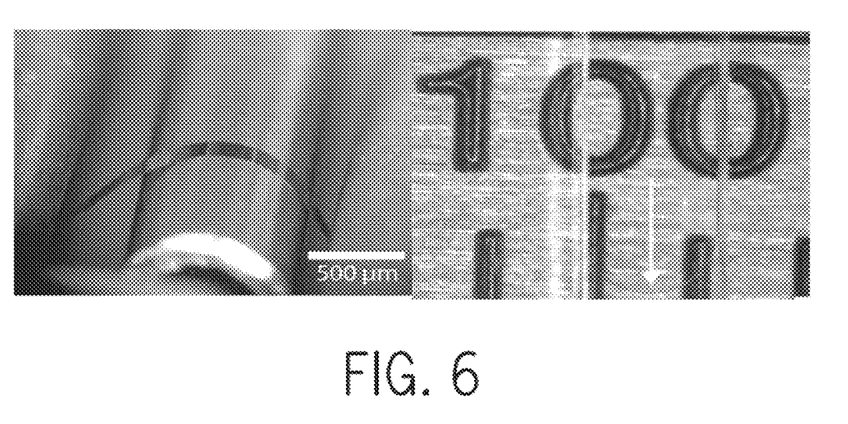
FIG. 6 illustrates, on the left, a 7 μm thick integrated circuit bending around a 1 mm diameter mandrel and, on the right, a micron-scale PECVD membrane with a 500 μm bend radius.

The resulting thin sheet or strip is flexible enabling the sheet or strip to be rolled up, deformed, or otherwise configured or shaped into geometries that are suitable for high volumetric density for a given surface area. As evidence of the flexibility of the formed sheet, the left image of FIG. 6 shows a 7 µm thick fully depleted silicon-on-oxide circuit with bending radii as small as 500 µm. Based on this fabrication process, the formed sheet or strip can be rolled into a glucose fuel cell with mm-scale inner radii dimensions enabling the fuel cells to achieve high volumetric power density with a small form factor.

A glucose fuel cell fabricated using the methods described above provides a power output that is sufficient to run micro-power and nano-power electronics. For example, the power budget needed for a 32-channel brain implant for paralysis powered by the disclosed fuel cell is summarized in Table I below.

TABLE I

| Function | Power |
|---|---|
| 32-channel adaptive sensing & amplification | 24 µW |
| 32-channel Decoding | 20 µW |
| Wireless Communication of kbs$^{-1}$ | 1 µW |
| Low-bandwidth stimulation | 25 µW |
| Voltage Boost and Voltage Regulation | 20 µW |
| Kbs$^{-1}$ Digital Control | 5 µW |
| Total Power | 95 µW |

To allow for variation in the glucose fuel cell output voltage, voltage regulation is incorporated into the circuitry, such that the chips are powered by a stable output voltage even if the output of the glucose fuel cell fluctuates over time. A power budget of 95 µW to power a brain implant for paralysis can be satisfied by the 320 µW output of the glucose fuel cell. Moreover, the power output provides a safety factor of three, allowing for the efficiency of the fuel cell to degrade over time while still safely powering the device. Thus, ultra-low-power electronics that can form a complete brain implant may be powered by our flexible glucose fuel cell.

In applications like epilepsy and cardiac pacemakers, the flexible glucose fuel cell output can trickle charge an ultracapacitor, which is then used for higher-power stimulation.

For example, epilepsy applications can be operated with seizure-dependent wakeups, and pacemaker stimulation can operate in a similar fashion. The mA current stimulation levels in a pacemaker exist for approximately 1 ms and arise from a charged capacitor, but they only occur every second or so, and only if normal beats are not detected.

There are various benefits and advantages that are provided by the disclosed glucose fuel cell.

The utilization of the flexible nature of the fabricated sheets or strips offers heretofore unheard of power generation in a solid state glucose fuel cell. The disclosed fuel cell enables the power budget for medical implants to be met by increasing volumetric power density by more than an order of magnitude. For example, the volumetric power density is increased by twenty times in the exemplary embodiment of FIG. 3. This increase in volumetric power density and the use of ultra-low-power electronics enable biological applications with safety factors in humans to be feasible in tightly constrained spaces of the body, which has not been possible before.

Moreover, the fabrication processes and methods for the flexible glucose fuel cell are based on semiconductor fabrication. Thus, the disclosed processes and methods enable the bioelectronics and fuel cell to all be manufactured on a single wafer and rolled up into one implantable device with a built-in, energy-harvesting power source. Furthermore, the use of traditional semiconductor fabrication enables scalability and mass manufacturability for several applications.

It is also notable that, unlike all prior systems which have focused on using blood plasma or interstitial-tissue environments for implantation, the preferred site of implantation is within the cerebrospinal-fluid-filled spaces in and around the brain and spinal cord, including the subarachnoid space, the cerebral ventricles, or the lumbar-cistern space of the central nervous system, though not necessarily so. These environments contain cerebrospinal fluid (CSF), which is almost cell free and has a highly reduced protein content, thus drastically reducing the chance of bio-fouling or cell encapsulation that have plagued prior glucose fuel cells. For example, 1 µl of blood plasma has approximately 5,000,000 erythrocytes, approximately 5,000 leukocytes, and approximately 150,000 to 450,000 thrombocytes with a protein concentration of approximately 7,000 mg/dL. In contrast, normal CSF has a cell count that is almost a million fold lower with respect to erythryocytes, 10,000 fold lower with respect to leukocytes, and 500,000 fold lower with respect to thrombocytes, and the overall protein concentration of CSF is almost 200 times lower than that of blood plasma. These several order of magnitude lower concentrations mean that the potential for biofouling or cell encapsulation is significantly lower in our intended site of implantation. Even if the input or output leads arise from less implant-friendly locations such as cardiac ventricles or brain interstitial tissue, the site of implantation of such electronics and the fuel source can be in relatively benign locations where CSF is abundant.

Indeed, the combination of flexibility and the use of an Ommaya reservoir enable a thin and flexible glucose fuel cell to be folded into a subcutaneous implant all along the spine or on top of the skull. Alternatively, a flexible glucose fuel cell can be implanted directly into a space in the lumbar cistern of the spine, or into ventricular or subarachnoid spaces of the brain.

It should be appreciated that various other modifications and variations to the preferred embodiments can be made within the spirit and scope of the invention. Therefore, the invention should not be limited to the described embodiments. To ascertain the full scope of the invention, the following claims should be referenced.

What is claimed is:

1. An enzyme-free, fully implantable glucose fuel cell for reception into a given constrained volume of implantation in a vertebrate in which the glucose fuel cell has access to fluid including glucose and dissolved fluidic oxygen, the fuel cell comprising:
   an anode adapted to oxidize the glucose with no biological enzymes or biological catalysts;
   a cathode adapted to reduce an oxidant with no biological enzymes or biological catalysts; and
   a membrane disposed between the anode and the cathode and separating the anode from the cathode;
   wherein the fuel cell is in the form of a flexible sheet that is geometrically deformed into a coiled or spiral shape receivable into the given constrained volume of implantation and wherein the flexibility is exploited to improve volumetric power density; and
   wherein the flexible sheet includes openings from one side of the flexible sheet to the other side of the flexible sheet that accommodate fluid flow of fluid containing dissolved glucose and dissolved fluidic oxygen from one side of the flexible sheet to the other side of the flexible sheet to increase overall availability of dissolved glucose and dissolved fluidic oxygen to the anode and cathode, respectively, and to allow either or both dissolved glucose and dissolved oxygen radial access between multiple coiled layers of the flexible sheet.

2. The glucose fuel cell of claim 1, wherein the flexible sheet further comprises a flexible mechanical substrate on which the anode, the cathode, and the membrane reside.

3. The glucose fuel cell of claim 2, wherein the flexible sheet is approximately 7 µm thick.

4. The glucose fuel cell of claim 2, wherein the flexible mechanical substrate is an oxide layer.

5. The glucose fuel cell of claim 1, wherein the flexible sheet is rolled such that the glucose fuel cell has a rolled-up form factor.

6. The glucose fuel cell of claim 1, wherein, as the flexible shape is deformed into a shape, the volumetric power density of the fuel cell is increased.

7. The glucose fuel cell of claim 1, wherein the anode is nanoporous platinum or platinized platinum, the cathode is a sulfonated tetrafluoroethylene-based fluoropolymer-copolymer having single-walled carbon nanotubes embedded therein, and the membrane is a sulfonated tetrafluoroethylene-based fluoropolymer-copolymer.

8. The glucose fuel cell of claim 1, wherein the oxidant is another carbohydrate or organic fuel.

9. The glucose fuel cell of claim 1, wherein a given constrained volume of implantation is a subcutaneous reservoir with access to cerebrospinal fluid in at least one of the brain and spinal cord of the vertebrate.

10. The glucose fuel cell of claim 1, wherein the fuel cell is used to sense glucose.

11. An implantable assembly comprising the glucose fuel cell of claim 1 and electronics powered by the glucose fuel cell, wherein the glucose fuel cell is co-fabricated with at least a portion of the electronics on a flexible mechanical substrate with semiconductor fabrication techniques that are common to both the electronics and to the glucose fuel cell.

12. The implantable assembly of claim 11, wherein the glucose fuel cell provides at least one of power and glucose-sensing inputs to a medical device.

13. The implantable assembly of claim 12, wherein the medical device is implanted alongside the glucose fuel cell.

14. The implantable assembly of claim 12, wherein the medical device is implanted within the vertebrate at a location remote from a location of implantation of the glucose fuel cell.

* * * * *

UNITED STATES PATENT AND TRADEMARK OFFICE
CERTIFICATE OF CORRECTION

PATENT NO. : 10,297,835 B2  
APPLICATION NO. : 14/278478  
DATED : May 21, 2019  
INVENTOR(S) : Sarpeshkar et al.

Page 1 of 1

It is certified that error appears in the above-identified patent and that said Letters Patent is hereby corrected as shown below:

In the Specification

In Column 1, Lines 11-15, delete:
"This invention was made with Government support under Grant No. R01 NS056140 awarded by the National Institutes of Health and by Grant No. 1332250 awarded by the National Science Foundation. The United States Government has certain rights in the invention."

And insert:
-- This invention was made with government support under NS056140 awarded by the National Institutes of Health, 1332250 awarded by the National Science Foundation, and FA8721-05-C-0002 awarded by the U.S. Air Force. The government has certain rights in the invention. --

Signed and Sealed this
Fourth Day of November, 2025

John A. Squires
*Director of the United States Patent and Trademark Office*